(12) United States Patent
Feldman

(10) Patent No.: US 7,002,695 B2
(45) Date of Patent: Feb. 21, 2006

(54) DUAL-SPOT PHASE-SENSITIVE DETECTION

(75) Inventor: Haim Feldman, Nof-Ayalon (IL)

(73) Assignee: Applied Materials Inc., Santa Clara, CA (US)

( * ) Notice: Subject to any disclaimer, the term of this patent is extended or adjusted under 35 U.S.C. 154(b) by 0 days.

(21) Appl. No.: 10/141,632

(22) Filed: May 7, 2002

(65) Prior Publication Data

US 2003/0210405 A1 Nov. 13, 2003

(51) Int. Cl.
*G01B 9/02* (2006.01)
(52) U.S. Cl. ..................................... 356/516
(58) Field of Classification Search ................ 356/516, 356/489, 511
See application file for complete search history.

(56) References Cited

U.S. PATENT DOCUMENTS

| 3,796,495 A | 3/1974 | Laub | 356/489 |
| 3,851,951 A | 12/1974 | Eveleth | 359/286 |

*Primary Examiner*—Samuel A. Turner
(74) *Attorney, Agent, or Firm*—Blakely Sokoloff Taylor & Zafamn LL

(57) ABSTRACT

Apparatus for optical assessment of a sample includes a radiation source, adapted to generate a beam of coherent radiation, and traveling lens optics, adapted to focus the beam so as to generate first and second spots on a surface of the sample and to scan the spots together over the surface. Collection optics are positioned to collect the radiation scattered from the first and second spots and to focus the collected radiation so as to generate a pattern of interference fringes. A detector detects a change in the pattern of the interference fringes as the spots are scanned over the surface.

24 Claims, 4 Drawing Sheets

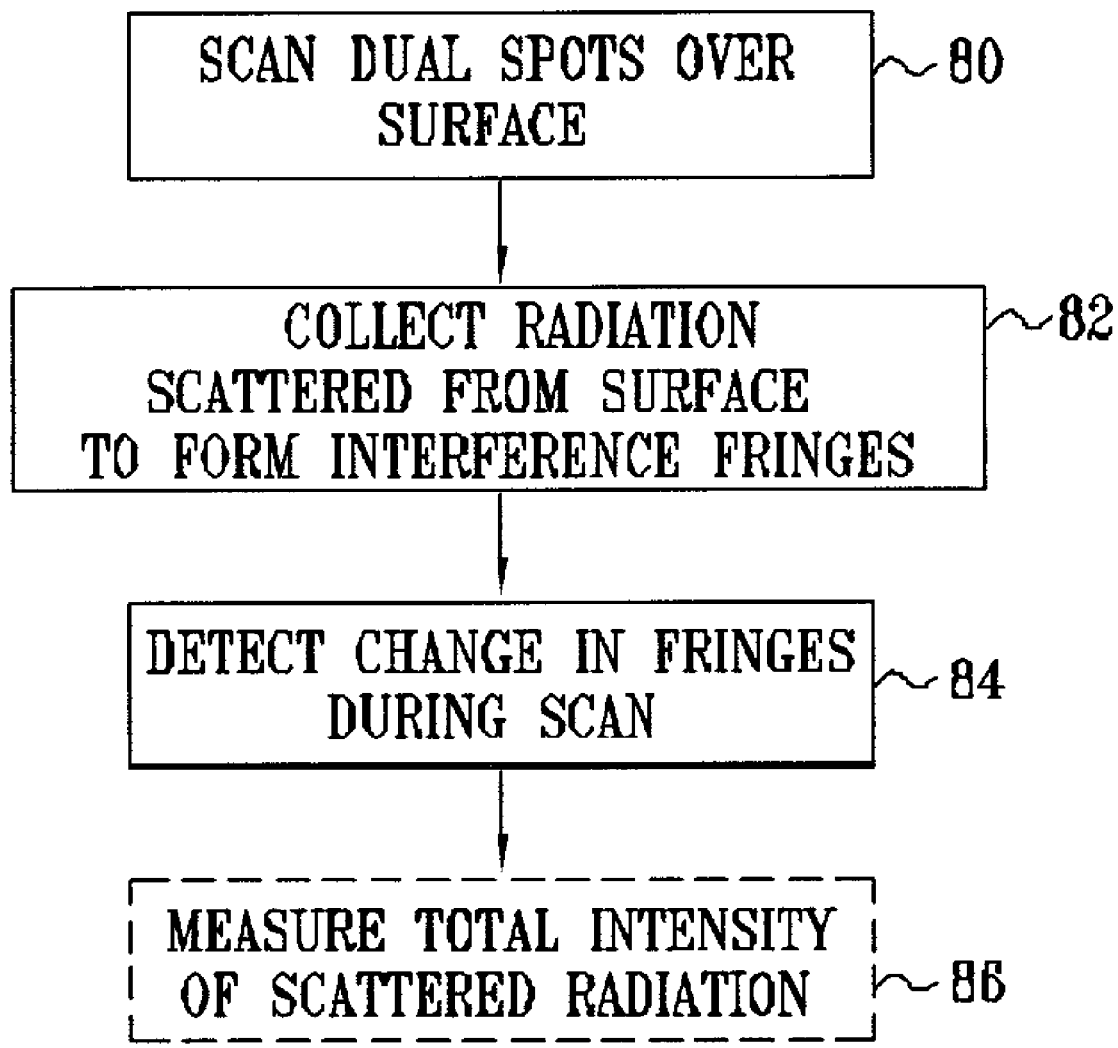

DUAL-SPOT PHASE-SENSITIVE DETECTION

FIELD OF THE INVENTION

The present invention relates generally to laser scanning systems, and specifically to methods and systems for optical inspection of substrates based on laser scanning.

BACKGROUND OF THE INVENTION

It is known in the art of microscopy to observe phase variations in an image of a sample in order to enhance detection of features that would otherwise be difficult to see. For example, methods of differential interference contrast (DIC) microscopy are described by M. Bass, E. W. Van Stryland, D. R. Williams, W. L. Wolfe in *HandBook of Optics II* (Second Edition, McGraw Hill, 1995), pages 17.28–17.36, which are incorporated herein by reference. DIC microscopy provides a monochromatic shadow cast image that effectively displays the gradient of optical paths. Those regions of the sample where the optical paths increase along a certain reference direction appear brighter, while those where the path differences decrease appear in reverse contrast. Image contrast is greater the steeper the gradient of path differences. DIC methods are useful for highlighting features such as very thin filaments and sharp interfaces, and show differences in local refractive index, as well as changes in surface elevation.

Traveling lens acousto-optic devices are also known in the art. A device of this sort is described, for example, by Eveleth in U.S. Pat. No. 3,851,951, whose disclosure is incorporated herein by reference. An acoustic transducer is coupled to one end of an acousto-optic Bragg cell. The acoustic transducer generates frequency-modulated acoustic pulses in the Bragg cell, which travel from one end of the cell to the other. The resulting spatial frequency variation of the traveling acoustic pulse causes a laser beam that passes through the pulse area to be focused onto an image plane. As the acoustic pulse travels from one end of the Bragg cell to the other, it acts as a traveling lens, causing the focused laser spot to be scanned across the image plane.

SUMMARY OF THE INVENTION

It is an object of some aspects of the present invention to provide improved methods and systems for optical inspection of a sample by laser scanning, and particularly for sensing phase variations in the laser radiation that is scattered from the sample.

In preferred embodiments of the present invention, a traveling lens device is used to focus a laser beam so as to generate and scan a pair of closely-spaced focal spots across the surface of a sample. Preferably, the traveling lens device comprises an acousto-optic Bragg cell, as described above, and the two focal spots are created by generating two closely-spaced (typically overlapping) acoustic pulses, which travel through the Bragg cell together. The light scattered from the two spots on the surface of the sample creates a pattern of interference fringes, wherein the position of the fringes shifts as a function of the phase difference between the two scattered beams. A detector measures the shift in order to determine a spatial gradient of phase changes over the surface.

Preferably, to measure the shift of the fringes, a beam stop having the form of a grid, with a period equal to the period of the interference fringes, is positioned in front of the detector. The grid is adjusted so that for a given reference phase difference between the beams (typically in a smooth area of the surface), the bright fringes are blocked. Then, as the two spots are scanned together over the sample, the optical signal received by the detector is proportional to the relative phase difference between the spots.

There is therefore provided, in accordance with a preferred embodiment of the present invention, apparatus for optical assessment of a sample, including:

a radiation source, adapted to generate a beam of coherent radiation;

traveling lens optics, adapted to focus the beam so as to generate first and second spots on a surface of the sample and to scan the spots together over the surface;

collection optics, positioned to collect the radiation scattered from the first and second spots and to focus the collected radiation so as to generate a pattern of interference fringes; and a detection unit, adapted to detect changes in the pattern of the interference fringes.

Preferably, the traveling lens optics include an acousto-optic Bragg cell and an acoustic transducer coupled to the cell so as to produce first and second frequency-modulated acoustic pulses, which travel along a length of the cell, such that when the beam of radiation passes through the cell, it is focused by the first and second pulses so as to generate and scan the first and second spots, respectively. Further preferably, the transducer is controllable so as to vary a relative timing and phase of the acoustic pulses, thereby controlling a spacing and relative phase of the first and second spots. Most preferably, the timing of the acoustic pulses produced by the transducer is controllable so as to vary a spatial period of the interference fringes, in order to facilitate detection of the shift in the fringes by the detector.

Preferably, the detection unit includes a detector, which is adapted to generate an output signal responsive to the change in the pattern of the interference fringes, and a signal processor, which is coupled to receive and process the output signal so as to derive therefrom a spatial gradient of phase changes in the radiation scattered from the surface, which is indicative of variations in elevation over the surface of the sample.

Typically, the interference fringes include bright and dark fringes that alternate with a fringe period, and the collection optics preferably include a beam stop, which is configured and positioned so that in a reference position of the fringes, the beam stop blocks the bright fringes from impinging on the detector. Most preferably, the beam stop includes a grid whose period is substantially equal to the fringe period. Additionally or alternatively, the detector includes a first detector, which is positioned so that the radiation not blocked by the beam stop impinges on the first detector, and the apparatus includes a second detector, which is positioned so that at least a portion of the radiation that is blocked by the beam stop impinges on the second detector, so as to provide a measure of a total intensity of the radiation scattered from the first and second spots. Preferably, the beam stop is adapted to reflect the portion of the radiation that it blocks from impinging on the first detector, and the second detector is positioned so that the reflected radiation impinges on the second detector.

Preferably, the traveling wave optics are adapted to focus the beam so that the spots have a predetermined spot width, and so that the spots are separated by a distance between about three and five times the spot width.

In a preferred embodiment, the traveling lens optics include an acousto-optic Bragg cell and an acoustic transducer coupled to the cell so as to produce a frequency-modulated acoustic pulse, which travels along a length of the cell, such that when the beam of radiation passes through the cell, it is focused and scanned by the acoustic pulse, and an optical splitter, which is configured to split the beam that is focused and scanned by the acoustic pulse in the Bragg cell, so as to generate the first and second spots on the surface.

There is also provided, in accordance with a preferred embodiment of the present invention, a method for optical assessment of a sample, including:

focusing a beam of coherent radiation so as to generate first and second spots on a surface of the sample and to scan the spots together over the surface;

collecting the radiation scattered from the first and second spots and focusing the collected radiation so as to generate a pattern of interference fringes; and detecting a shift in the interference fringes as the spots are scanned over the surface.

The present invention will be more fully understood from the following detailed description of the preferred embodiments thereof, taken together with the drawings in which:

BRIEF DESCRIPTION OF THE DRAWINGS

FIG. 4 is a flow chart that schematically illustrates a method for dual-spot scanning, in accordance with a preferred embodiment of the present invention.

DETAILED DESCRIPTION OF PREFERRED EMBODIMENTS

Figure 1:
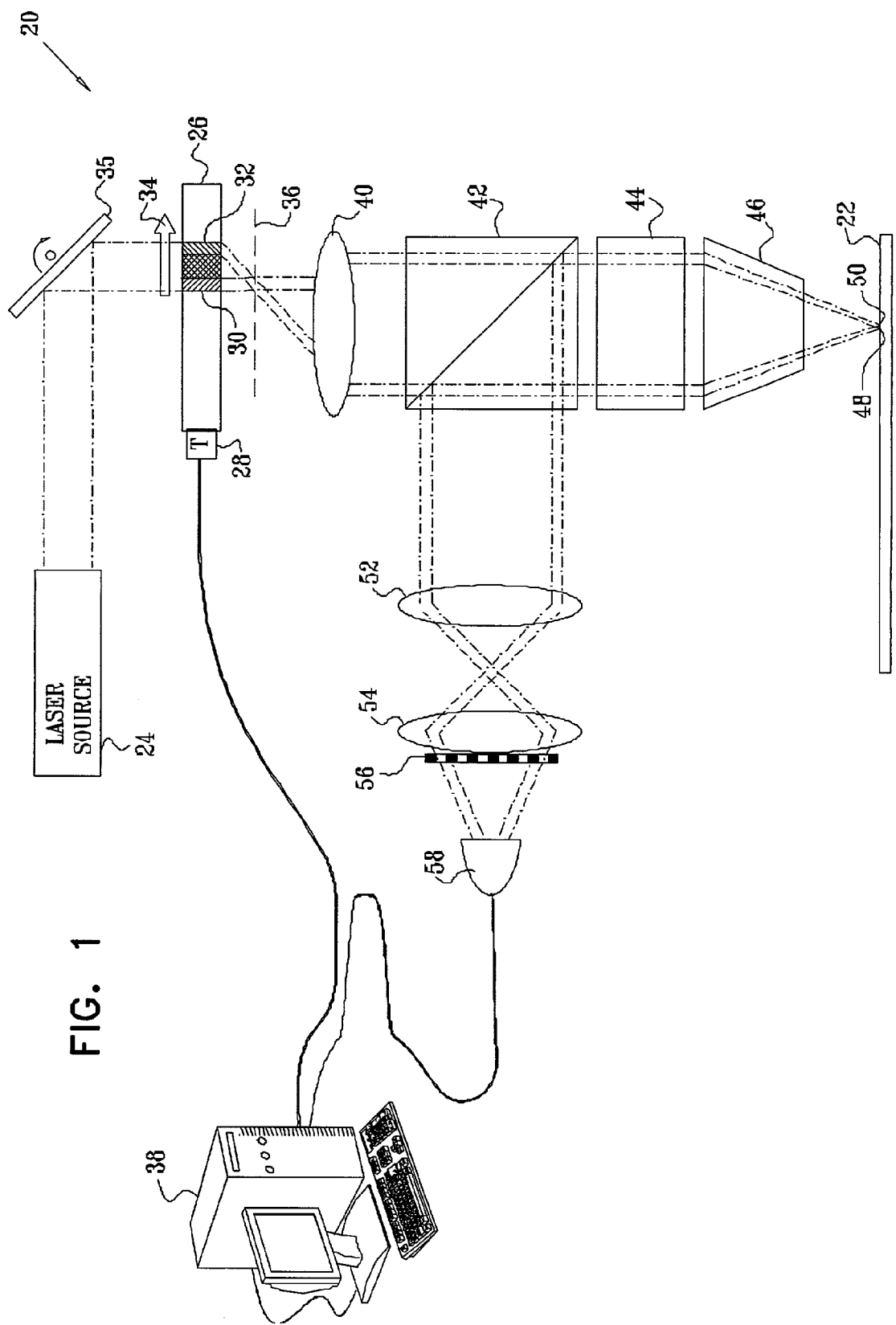
FIGS. 1–3 are schematic side views of a dual-spot optical scanning and detection system, in accordance with preferred embodiments of the present invention.

FIG. 1 is a schematic side view of a dual-spot optical scanning and detection system 20, in accordance with a preferred embodiment of the present invention. This system is typically used in automated, high-speed inspection of a sample 22, such as a semiconductor wafer. Alternatively, the principles embodied in system 20 may be applied in other areas of optical imaging, both in the reflective mode shown in the figures and in transmissive modes, as are known in the art. Systems of this sort are useful particularly in observing defects and pattern variations in semiconductor wafers and photomasks, as well as in other applications of optical phase-based detection, such as in scanning microscopy, including particularly confocal microscopy.

A laser source 24 outputs a laser beam, which is directed to pass through an acousto-optic Bragg cell 26. An acoustic transducer 28 applies two acoustic pulses to cell 26 in close succession, causing two traveling lenses 30 and 32 to travel from one end of the cell to the other, as indicated by an arrow 34. Preferably, cell 26 comprises a material that exhibits a strong acoustic effect on refractive index and weak acoustic attenuation, such as $TeO_2$, $LiNbO_3$, $SiO_2$ or $H_2O$, or other materials known in the art. Each of the two lenses focuses the laser beam to a respective spot in a focal plane 36. As lenses 30 and 32 travel through cell 26, these two spots scan rapidly along a line in the focal plane. Because the acousto-optic effect is linear, the two traveling lenses can overlap without substantially affecting the focusing properties of either lens. Optionally, the laser beam from source 24 is scanned over cell 26 by a pre-scanner 35, such as a scanning mirror or another acousto-optic cell, so that the laser beam tracks the traveling lenses.

A collection lens 40 collects the light from focal plane 36 and directs it through a beamsplitter 42. A telescope 44 and objective lens 46 then focus the light so as to create two spots 48 and 50 on the surface of sample 22. Objective lens 46 collects the light scattered from the two spots, creating an interference pattern of linear, bright and dark fringes at the exit pupil of the objective lens (which is typically defined by a beam stop in telescope 44, as is known in the art). The number of fringes is typically equal to twice the ratio of the spot separation to the spot width. The spot separation can be controlled by varying the relative timing of the acoustic pulses used to create traveling lenses 30 and 32. Preferably, the spots are separated by between about three and five spot widths, in order to give a small number of fringes while avoiding overlap between the spots. The positions of the fringes shift as spots 48 and 50 are scanned over sample 22 by lenses 30 and 32, in proportion to the phase difference between the light rays scattered from the two spots. Such phase differences typically arise due to local variations in the elevation of the surface (due to integrated circuit features or defects, for example), and possibly also due to variations in the refractive index of the surface material.

The light collected by objective lens 46 is directed by telescope 44 and beamsplitter 42 to a focusing telescope formed by lenses 52 and 54. These lenses are arranged to produce a conjugate image of the exit pupil of objective lens 46, at which the interference pattern is again in focus. A beam stop 56, having the form of a grid, is placed in the conjugate plane. The grid is chosen so that it has the same period as the interference pattern. Stop 56 is preferably positioned so that in a certain reference position of the fringes, the grid blocks the bright fringes of the interference pattern substantially completely. The reference position is most preferably chosen as the position of the fringes when spots 48 and 50 are located in a smooth area of the surface of sample 22, in which the phase difference between the spots is zero. If there is a mismatch between the period or phase of the interference pattern and that of the grid, the relative delay and phase of traveling lenses 30 and 32 can be adjusted in order to correct it by changing the signal input to transducer 28.

Light that passes through the grid of stop 56 is received by a detector 58, preferably a photomultiplier tube (although detectors of other types may also be used). As the position of the interference fringe pattern shifts due to phase differences over the surface of the sample, the intensity of the light passing through the grid and reaching the detector varies accordingly. Thus, the amplitude of the signal that is output by detector 58 is proportional to the relative phase shift between spots 48 and 50. This signal is processed by a signal processor 38 to form a high-contrast phase gradient image of the sample surface, in which edges and other variations of elevation are emphasized. Typically, processor 38 comprises a general-purpose computer, with suitable software and front-end circuits for interacting with detector 58 and other elements of system 20. Preferably, processor 38 also controls transducer 28 so as to adjust the properties of traveling lenses 30 and 32 as required.

Figure 2:
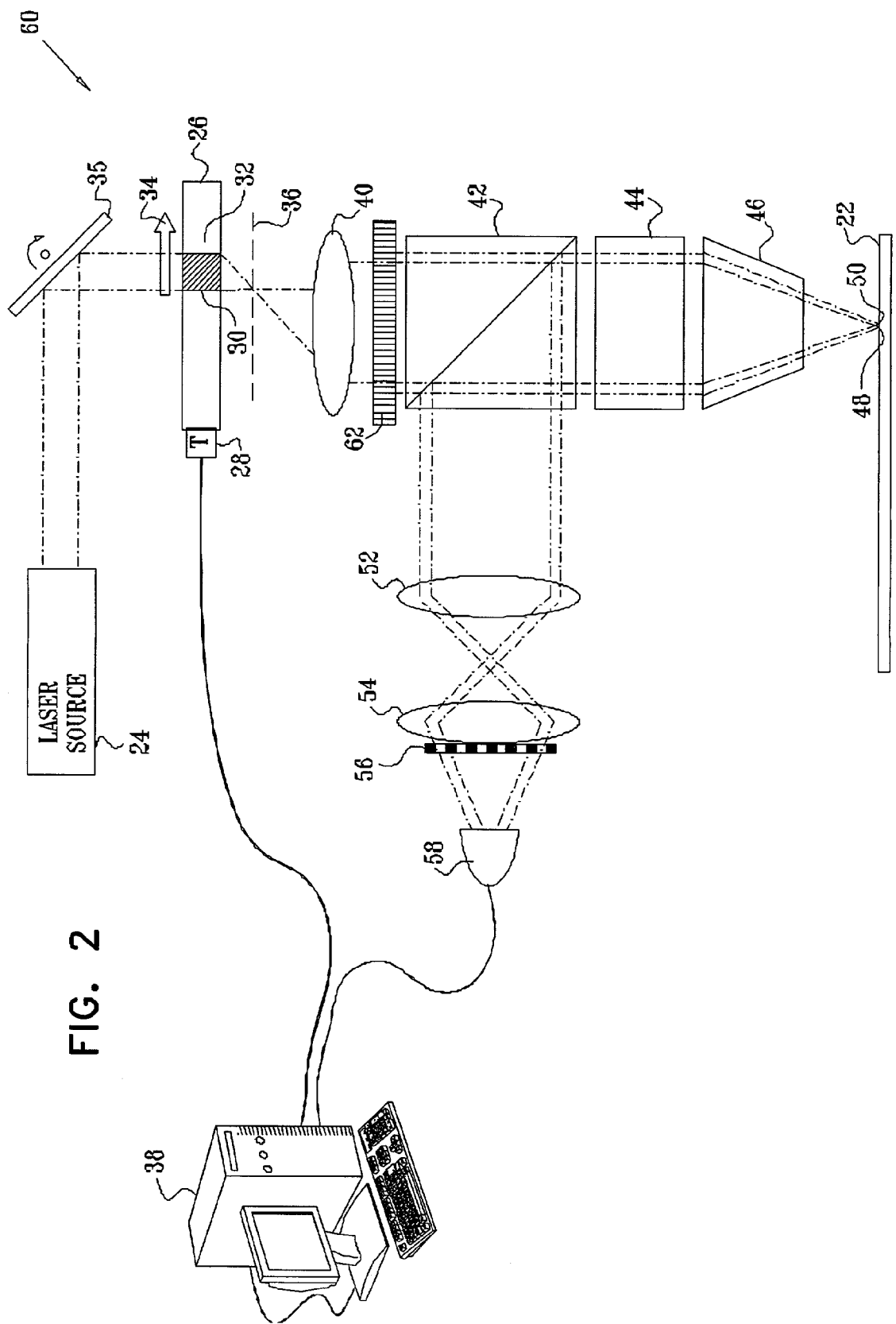

FIG. 2 is a schematic side view of system 60, in accordance with an alternative embodiment of the present invention. In this embodiment, transducer 28 generates only a single traveling lens 30 in Bragg cell 26. In order to generate both spots 48 and 50 on sample 22, an optical splitter 62, typically a diffractive element, such as a transmission grating, is inserted in the beam path as shown. Two closely-spaced diffraction orders provide the two spots. Alternatively, a birefringent element may be used in like manner to generate the two spots, in a manner similar to that used, for example, in the Nomarski microscope described in the above-mentioned *HandBook of Optics*. In other respects, the operation of this embodiment is substantially the same as the embodiment of FIG. 1. Of course, when only the single traveling lens is used, as in the embodiment of FIG. 2, the relative positions and phases of spots 48 and 50 cannot be so readily adjusted.

Figure 3:
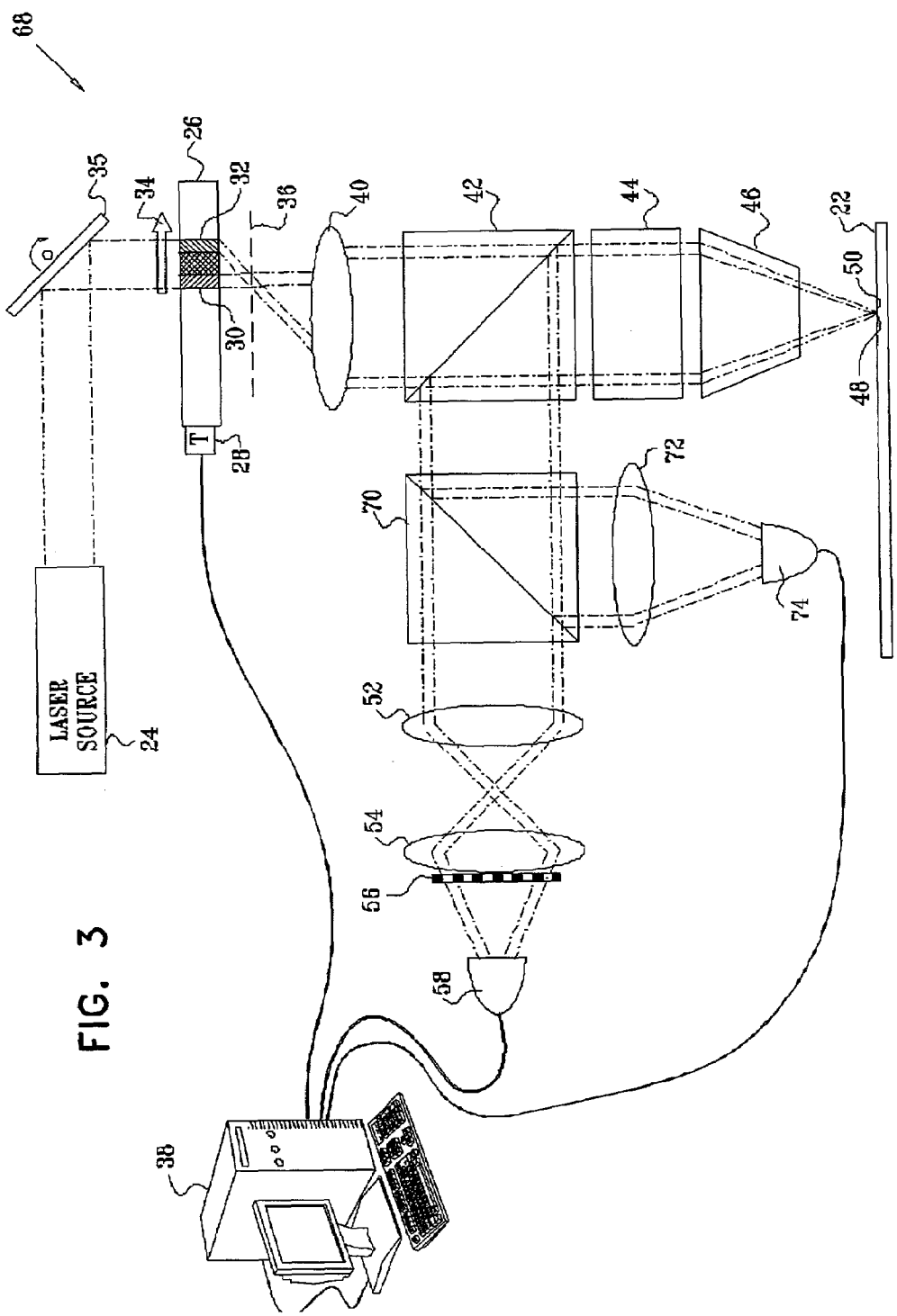

FIG. 3 is a schematic side view of system 68, in accordance with another alternative embodiment of the present invention. Here the light scattered from sample 22 is divided by a second beamsplitter 70, which directs a portion of the light to another detector 74, via an accompanying focusing lens 72. Detector 74 in this configuration generates a signal that is proportional to the total intensity of light scattered from the sample. Thus, while detector 58 measures specifically phase variations, due primarily to changes in elevation of the sample surface, detector 74 measures variations in the surface reflectivity. The separate measurement of phase and reflectivity characteristics of the surface are preferably combined by processor 38 to provide a precise, detailed diagnostic picture of the surface.

Alternatively, detector 74 may be positioned and configured, with suitable optics, to measure light that is reflected from stop 56. In this case, the sum of the signals output by detectors 58 and 74 gives a measure of the total scattered intensity from sample 22, without requiring the addition of beamsplitter 70.

FIG. 4 is a flow chart that schematically illustrates a method for dual-spot scanning and detection, in accordance with a preferred embodiment of the present invention, using the systems shown in FIGS. 1–3. The beam from laser source 24 is focused by the traveling lens or lenses in Bragg cell 26 so as to generate dual spots 48 and 50 on the surface of sample 22, and to scan the spots together over the surface, at a scanning step 80. The system optics collect the radiation scattered from the two spots, and focus the collected radiation so as to generate a pattern of interference fringes in a conjugate plane, at a collection step 82. The radiation is focused onto detector 58, preferably via stop 56. The detector and processor 38 together define a detection unit, which detects changes in the fringes as the spots scan over the surface, at a change detection step 84. Optionally, the total intensity of the scattered radiation is also measured, at an intensity measurement step 86, by detector 74 (FIG. 3), for example. Step 84 gives phase data, while step 86 gives reflectivity data, which are used together or separately to provide information about the surface of sample 22.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus for optical assessment of a sample, comprising:
    a radiation source, adapted to generate a beam of coherent radiation;
    traveling lens optics, adapted to focus the beam so as to generate first and second spots on a surface of the sample and to scan the spots together over the surface;
    collection optics, positioned to collect the radiation scattered from the first and second spots and to focus the collected radiation so as to generate a pattern of interference fringes; and
    a detection unit, adapted to detect changes in the pattern of interference fringes.

2. Apparatus according to claim 1, wherein the traveling lens optics comprise an acousto-optic Bragg cell and an acoustic transducer coupled to the cell so as to produce first and second frequency-modulated acoustic pulses, which travel along a length of the cell, such that when the beam of radiation passes through the cell, it is focused by the first and second pulses so as to generate and scan the first and second spots, respectively.

3. Apparatus according to claim 2, wherein the transducer is controllable so as to vary a relative timing and phase of the acoustic pulses, thereby controlling a spacing and relative phase of the first and second spots.

4. Apparatus according to claim 3, wherein the timing of the acoustic pulses produced by the transducer is controllable so as to vary a spatial period of the interference fringes, in order to facilitate detection of the shift in the fringes by the detector.

5. Apparatus according to claim 1, wherein the detection unit comprises:
    a detector, which is adapted to generate an output signal responsive to the change in the pattern of the interference fringes; and
    a signal processor, which is coupled to receive and process the output signal so as to derive therefrom a spatial gradient of phase changes in the radiation scattered from the surface.

6. Apparatus according to claim 5, wherein the spatial gradient is indicative of variations in elevation over the surface of the sample.

7. Apparatus according to claim 1, wherein the interference fringes comprise bright and dark fringes that alternate with a fringe period, and wherein the collection optics comprise a beam stop, which is configured and positioned so that in a reference position of the fringes, the beam stop blocks the bright fringes from impinging on the detector.

8. Apparatus according to claim 7, wherein the beam stop comprises a grid whose period is substantially equal to the fringe period.

9. Apparatus according to claim 7, wherein the detector comprises a first detector, which is positioned so that the radiation not blocked by the beam stop impinges on the first detector, and comprising a second detector, which is positioned so that at least a portion of the radiation that is blocked by the beam stop impinges on the second detector, so as to provide a measure of a total intensity of the radiation scattered from the first and second spots.

10. Apparatus according to claim 9, wherein the beam stop is adapted to reflect the portion of the radiation that it blocks from impinging on the first detector, and wherein the second detector is positioned so that the reflected radiation impinges on the second detector.

11. Apparatus according to claim 1, wherein the traveling wave optics are adapted to focus the beam so that the spots have a predetermined spot width, and so that the spots are separated by a distance between about three and five times the spot width.

12. Apparatus according to claim 1, wherein the traveling lens optics comprise:
    an acousto-optic Bragg cell and an acoustic transducer coupled to the cell so as to produce a frequency-modulated acoustic pulse, which travels along a length of the cell, such that when the beam of radiation passes through the cell, it is focused and scanned by the acoustic pulse; and an optical splitter, which is configured to split the beam that is focused and scanned by the acoustic pulse in the Bragg cell, so as to generate the first and second spots on the surface.

13. A method for optical assessment of a sample, comprising:

focusing a beam of coherent radiation so as to generate first and second spots on a surface of the sample and to scan the spots together over the surface;

collecting the radiation scattered from the first and second spots and focusing the collected radiation so as to generate a pattern of interference fringes; and detecting changes in the pattern of the interference fringes.

14. A method according to claim 13, wherein focusing the beam of coherent radiation comprises applying first and second frequency-modulated acoustic pulses to an acousto-optic Bragg cell, so that the first and second pulses travel along a length of the cell, such that when the beam of radiation passes through the cell, it is focused by the first and second pulses so as to generate and scan the first and second spots, respectively.

15. A method according to claim 14, wherein applying first and second frequency-modulated acoustic pulses comprises varying a relative timing and phase of the acoustic pulses so as to control a spacing and relative phase of the first and second spots.

16. A method according to claim 15, wherein varying the relative timing and phase comprises controlling the timing so as to vary a spatial period of the interference fringes, in order to facilitate detection of the shift in the fringes by a detector.

17. A method according to claim 13, wherein detecting the shift comprises generating an output signal responsive to the change in the pattern of the interference fringes, and processing the output signal so as to derive therefrom a spatial gradient of phase changes in the radiation scattered from the surface.

18. A method according to claim 17, wherein the spatial gradient is indicative of variations in elevation over the surface of the sample.

19. A method according to claim 13, wherein the interference fringes comprise bright and dark fringes that alternate with a fringe period, and wherein detecting the change comprises positioning a beam stop so that in a reference position of the fringes, the beam stop blocks the bright fringes, and measuring the radiation that passes through the beam stop as the spots are scanned over the surface.

20. A method according to claim 19, wherein the beam stop comprises a grid whose period is substantially equal to the fringe period.

21. A method according to claim 19, and comprising measuring at least a portion of the radiation that is blocked by the beam stop, so as to provide a measure of a total intensity of the radiation scattered from the first and second spots.

22. A method according to claim 21, wherein the beam stop is adapted to reflect the portion of the radiation that it blocks from impinging on the first detector, and wherein measuring the portion of the radiation that is blocked comprises measuring the radiation reflected from the beam stop.

23. A method according to claim 13, focusing the beam comprises generating the spots with a predetermined spot width, and so that the spots are separated by a distance between about three and five times the spot width.

24. A method according to claim 13, wherein focusing the beam comprises:

applying a frequency-modulated acoustic pulses to an acousto-optic Bragg cell, so as to produce a frequency-modulated acoustic pulse, which travels along a length of the cell, such that when the beam of radiation passes through the cell, it is focused and scanned by the acoustic pulse; and splitting the beam that is focused and scanned by the acoustic pulse in the Bragg cell, so as to generate the first and second spots on the surface.

* * * * *